(12) United States Patent
Jarekrans et al.

(10) Patent No.: US 6,309,862 B1
(45) Date of Patent: Oct. 30, 2001

(54) METHIONINE CONTAINING ANIMAL CELL CULTURE MEDIUM AND ITS USE

(75) Inventors: Mats Jarekrans, Umeå; Hans Olovsson, Sundsvall, both of (SE)

(73) Assignee: Bionative AB, Umeå (SE)

(*) Notice: Subject to any disclaimer, the term of this patent is extended or adjusted under 35 U.S.C. 154(b) by 0 days.

(21) Appl. No.: 09/647,402

(22) PCT Filed: Mar. 23, 1999

(86) PCT No.: PCT/SE99/00453
§ 371 Date: Nov. 17, 2000
§ 102(e) Date: Nov. 17, 2000

(87) PCT Pub. No.: WO99/50399
PCT Pub. Date: Oct. 7, 1999

(30) Foreign Application Priority Data

Mar. 30, 1998 (SE) .................................................. 9801090

(51) Int. Cl.$^7$ .............................. C12N 5/00; C12P 21/04; C12P 21/06
(52) U.S. Cl. ..................... 435/70.1; 435/68.1; 435/404
(58) Field of Search .................................. 435/70.1, 405, 435/68.1

(56) References Cited

U.S. PATENT DOCUMENTS

| | | |
|---|---|---|
| 4,696,899 | 9/1987 | Tóth . |
| 4,767,704 | 8/1988 | Cleveland et al. . |
| 5,358,708 | 10/1994 | Patel . |
| 5,676,942 | 10/1997 | Testa el al. . |

FOREIGN PATENT DOCUMENTS

WO92/15614   9/1992  (WO) .

OTHER PUBLICATIONS

Cantell et al. (1981) Methods in Enzymology 78: 29–38.*

Eagle, Harry. Science (1959) 130: 432–437.*

1.Chemical Abstracts, vol. 128, Shih–Tsung Wang et al. Abstract No. 34151, J. Nutr. 1997, 127 (11), pp. 2135–2141.

Kari Cantell, (1979) Why is Interferon Not in Clinical Use Today?, in *Interferon 1 1979*, (I Gresser, ed.) p.1–28 (Academic Press: New York).

* cited by examiner

Primary Examiner—Kenneth R. Horlick
Assistant Examiner—Alexander H. Spiegler
(74) Attorney, Agent, or Firm—Burns, Doane, Swecker & Mathis, L.L.P.

(57) ABSTRACT

A nutrient medium for protein producing cells, characterized in that said medium consists essentially of the following components: a physiological saline containing $Ca^{2+}$, $K^+$, $Mg^{2+}$ and $Na^+$, an energy source, a pH buffer and methionine in an amount of 0.015–2.0 g/liter, and optionally antibiotics. The invention further relates to use of the nutrient medium for cells and human leukocytes.

18 Claims, 2 Drawing Sheets

EB122-054-04, Reference ( BNL medium)

Figure 1:
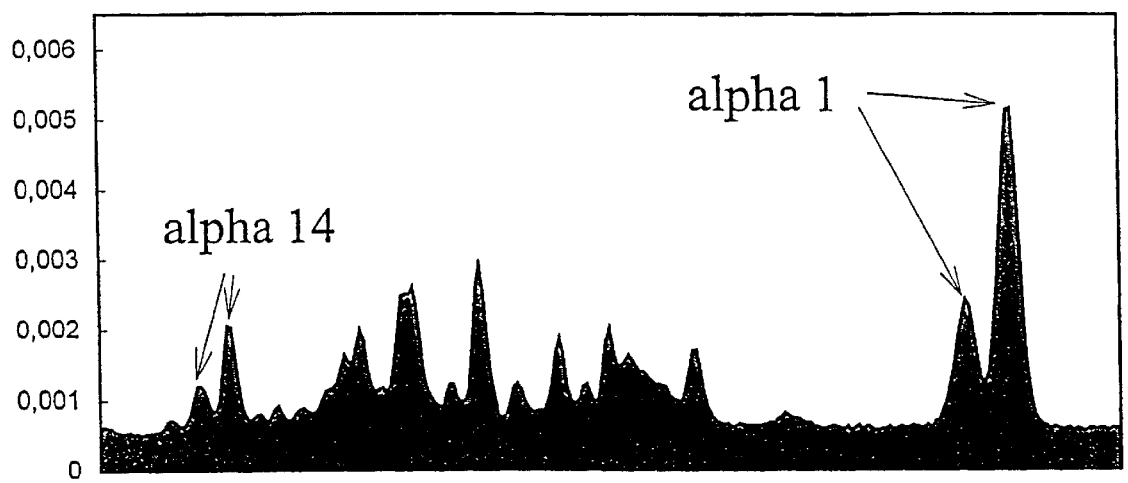
Figure 1:
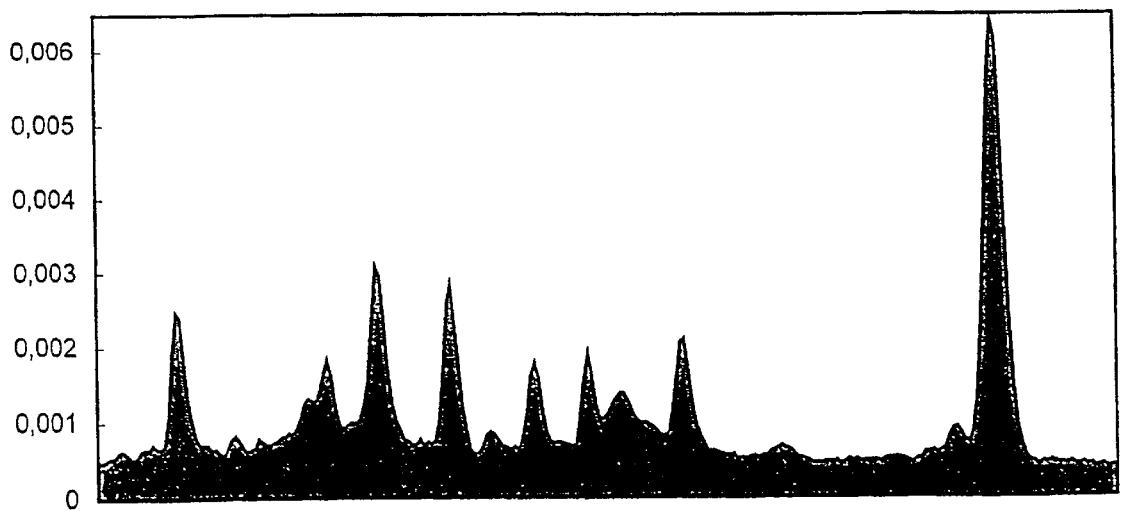

EB122-054-03, 500 mg Methionine / l
added to the medium

EB122-054-401, 500 mg Methionine / l added to the medium

EB122-054-403, 500mg Methionine / l added when harvesting

METHIONINE CONTAINING ANIMAL CELL CULTURE MEDIUM AND ITS USE

This application claims the benefit of U.S. provisional application Ser. No. 60/085,392, filed May 16, 1998.

FIELD OF THE INVENTION

The present invention relates to nutritive mediums for animal cells and specifically to a nutritive medium for human leukocytes.

BACKGROUND OF THE INVENTION

Usually animal cells are cultured in media, containing all necessary amino acids, vitamins, an energy source e.g. glucose and a balanced salt solution. The media can also contain trace amounts of different hormones such as insulin. The different components in the media can be altered depending on cell type and also the amount of the different components can be altered depending on the intended use. Some of these media are commercially available such as EMEM (Eagle's Minimum Essential Medium) which is well suited for a broad spectrum of mammalian cells, RPMI 1640, which was originally formulated for suspension cultures or monolayer cultures of human leukaemic cells, and DMEM (Dulbecco's Modified Eagle's Media) also well suited for broad spectrum of mammalian cells. In many cases, sera such as bovine serum and the like are added thereto. The addition of for example bovine serum is often necessary for accomplishing the desired growth and viability of the cultured cells.

Often, desired products are secreted from the cells and following a purification procedure the desired product secreted from the cells may be obtained in a sufficiently pure form. The purity of the end-products are always depending of the purity of the starting material. By using a purer, less complex starting material, in this case the medium, the purified end product will then become purer compared to using a more complex medium.

PRIOR ART

One way to improve the purity of the end product is to use a more simplified media which has been described in inter alia U.S. Pat. No. 4,696,899. This patent describes the manufacture of interferon-alpha and interferon-gamma from leukocytes using a simplified media.

The use of methionine as a component in serum free media for culturing animal cells is disclosed in EP0 501 435, which teaches the addition of methionine in an amount of 8.0 to 14.0 mg/l. Both higher and lower concentrations are rejected as lacking the desired effect.

The use of methionine in the formulation of polypeptide products for pharmaceutical or therapeutical use is known. Methionine is added to inhibit the oxidation of methionine residues with such polypeptides. According to U.S. Pat. No. 5,272,135 me thionine is added to a recombinant human epidermal growth factor (rhEGF) formulation in amounts ranging from 0.01 to 0.3% (w/v) or in a ratio of 10:1–100:1 to the methionine residues within the protein.

Further U.S. Pat. No. 5,358,708 describes the addition of methionine for the stabilisation of interferon formulations in an amount of 2 mg/ml or in a ratio of methionine to protein component of 10:1–100:1.

SUMMARY OF THE INVENTION

The present inventors have surprisingly shown that a nutritive medium with a highly reduced number of ingredients but with the addition of methionine in amounts exceeding any previously reported amounts allows for an unchanged or even slightly increased yield of interferon together with a pronounced improvement in end product homogeneity, stability and a striking simplification of the preparation of the media resulting in economical benefits.

According to the invention there is provided a nutrient medium for protein producing cells. Said medium consists essentially of the following components: an aqueous physiological saline solution containing $Ca^{2+}$, $K^+$, $Mg^{2+}$ and $Na^+$, an energy source, a pH buffer and methionine in an amount of 0.015–2.0 g/liter, and optionally antibiotics.

Preferred nutrient media have the following compositions:

A nutrient medium as described, characterized in that the medium has the following composition (g/l):

| | |
|---|---|
| $CaCl_2 \times 2H_2O$ | 0.13–0.35 |
| KCl | 0.2–0.5 |
| $MgCl_2 \times 6H_2O$ | 0–0.5 |
| NaCl | 5.0–8.0 |
| $NaH_2PO_4 \times 2H_2O$ | 0–0.15 |
| Glucose | 1.0–7.0 |
| Tricine | 1.5–3.0 |
| $NaHCO_3$ | 0.5–3.0 |
| Neomycin 10% | 0–0.25 |
| Methionine | 0.015–2.0, and |
| Agamma-plasma | 1.0–10 % (v/v). |

A nutrient medium as described, characterized in that the medium has the following composition (g/l):

| | |
|---|---|
| $CaCl_2 \times 2H_2O$ | 0.13–0.2 |
| KCl | 0.2–0.4 |
| $MgCl_2 \times 6H_2O$ | 0–0.2 |
| NaCl | 6.8–8.0 |
| $NaH_2PO_4 \times 2H_2O$ | 0–0.105 |
| Glucose | 1.0–5.0 |
| Tricine | 1.5–3.0 |
| $NaHCO_3$ | 0.75–1.0 |
| Neomycin 10% | 0–0.25 |
| Methionine | 0.015–2.0, and |
| Agamma-plasma | 3.0–5 % (v/v). |

A nutrient medium as described above but with a methionine content of 0.050–2.0 g/l.

A nutrient medium as described above but with a methionine content of 0.050–0.100 g/l.

A nutrient medium as described, characterized in that the medium has the following composition (g/l):

| | |
|---|---|
| $CaCl_2 \times 2H_2O$ | 0.2 |
| KCl | 0.4 |
| $MgCl_2 \times 6H_2O$ | 0.2 |
| NaCl | 6.8 |
| $NaH_2PO_4 \times 2H_2O$ | 0.105 |
| Glucose | 5.0 |
| Tricine | 1.5 |
| $NaHCO_3$ | 0.75 |
| Neomycin 10% | 0.25 |
| Methionine | 0.75, and |
| Agamma-plasma | 4% (v/v). |

Another aspect of the invention is use of the nutrient medium for animal cells or human leukocytes. In a preferred embodiment the medium is used in a production process for interferon.

In comparison to the conventional and well known Eagle's Minimal Essential Medium (EMEM) the inventive medium totally lacks the amino acid stock solution, the vitamin solution and folic acid solution, constituting integrated parts of EMEM.

On the other hand, compared to the so called Cantell medium, first disclosed by Cantell et al. in 1981 (Methods in Enzymology, vol. 78, 1981) and commonly used for the incubation of human leukocytes, the inventive medium contains $MgCl_2$, $NaH_2PO_4$ but lacks L-glutamine. In their original work, Cantell et al. report that experiments aimed at identifying those ingredients in EMEM needed for optimum yields of interferon give conflicting results (see Example 2).

With this background, it is even more surprising that the inventive medium not only allows for the production of interferon with unreduced yields in comparison with EMEM. It also produces a marked improvement in yield in comparison with other simplified media. In addition, the less complex medium facilitates purification of the desired product and gives pronounced process economical benefits as the medium is easier to prepare and contains fewer media components to order, register and analyse etc. Moreover, the inventive medium, gives a more homogenous and more stable product with maintained yield.

The invention is also applicable on other types of cells since the invention is of a general nature. For growing cells, this is not the ideal medium but in a stationary phase or protein producing phase this medium gives many advantages as mentioned above. Thus, the invention can be applied on other protein-producing cells/cell-lines.

The main components in the inventive medium are $CaCl_2$, a pH-buffer, an energy source, KCl, NaCl and methionine. The exact amount of each component is depending on the cell concentration used. A high cell concentration implies that more of or most of the components are needed, except for NaCl which has to be decreased in order to establish a physiological medium. Tricine is often used in cell cultures together with $NaHCO_3$ in order to keep the pH in an acceptable range. In the inventive process this range is between 7.0–8.0, most preferred 7.5, otherwise the viability and interferon yield will decrease. Other kinds of pH-buffers may also be used as long as they are non-toxic for the leukocytes. $Ca^{2+}$ has to be present in the medium, otherwise the interferon yield will become very low. Glucose is the cheapest energy source and it is also rapidly metabolized by the leukocytes. Therefore, it is well suited for these kinds of processes but other monosaccharides or disaccharides may function as well. Surprisingly we found that methionine had a very positive effect on the product when it is present in the medium. It seems to minimize the oxidation of the interferon-alpha proteins during the incubation and it also improves the stability of the harvested crude interferon and thereby the purified final product is also improved. The amount of methionine used, as mentioned earlier is dependent on the cell concentration. A too low amount will result in decreased effect and too high an amount will cause lower interferon yields. About 75 mg methionine per liter has been found to work well for leukocyte concentrations between $6 \times 10^9$ and $10 \times 10^9$, and a range of about 50 to 100 mg/liter is an especially preferred range.

The invention is further illustrated by the following examples. Various modifications can be made without departure from the spirit and scope of the invention. Accordingly, it is not intended that the invention be limited except as by the intended claims.

SHORT DESCRIPTION OF THE DRAWINGS

Figure 2:
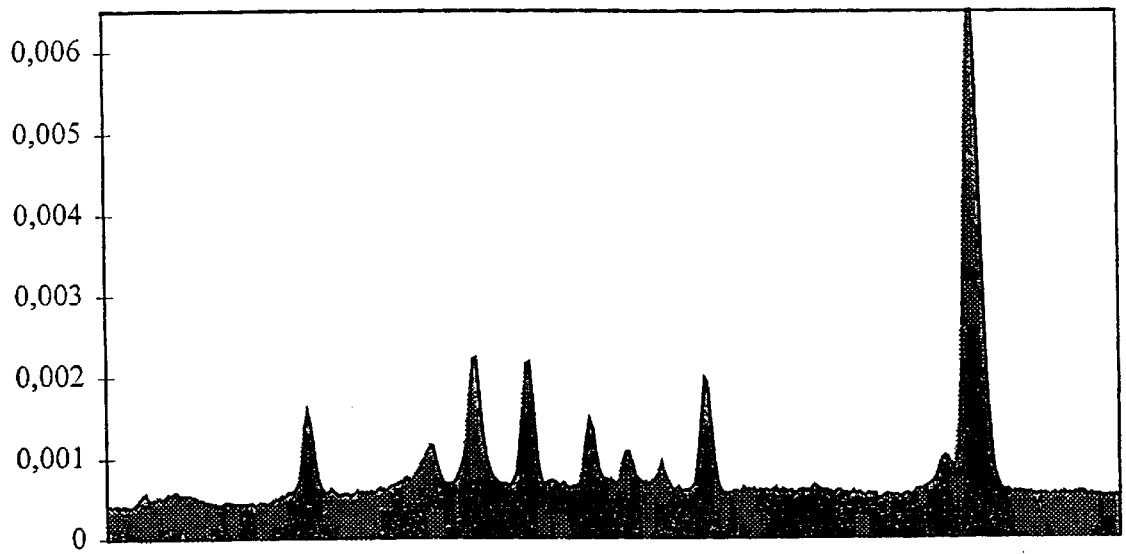
Figure 2:
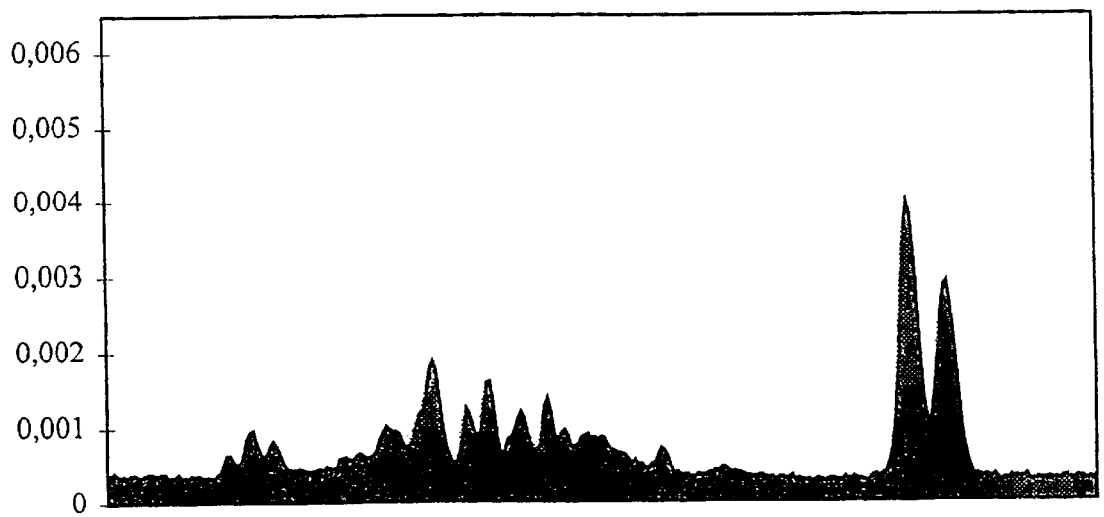

The present invention will be described in closer detail in the following description and examples with reference to the attached drawings, in which FIG. 1 shows the HPLC chromatogram (subtype pattern) from purified interferon alpha proteins obtained from medium supplemented with 500 mg/l of L-methionine (lower panel) in comparison with interferon proteins purified from medium without L-methionine (upper panel),and FIG. 2 shows also the HPLC peak-pattern (sub-type pattern) of the purified interferon-alpha proteins using the HPLC-method but this time the addition of 500 mg/l of L-methionine, added to the media before addition of leukocytes is compared with the addition of 500 mg/l of L-methionine added directly after incubation.

EXAMPLES

In the examples, the following abbreviations will be used: BNLM—the inventive medium; BNL—the inventive medium without L-methionine; GIBCO-EMEM manufactured by GIBCO; EMEM-EMEM manufactured according to Cantell (K. Cantell, S. Hirvonen, H.-L. Kauppinen, G. Myllylä, Methods of Enzymology, Vol. 78, p. 29–38, Academic Press, 1981) with phosphate and an increased amount of glucose (5 g/l); CM-simple media according to Cantell (H.-L. Kauppinen, G. Myllylä, and K. Cantell in "Human Interferon" (W. R. Stinebring and P. J. Chapple, eds.), p. 1 Plenum, New York, 1978); CMV-simple media according to Cantell (1978) but without L-glutamine, decreased amounts of Tricine and $NaHCO_3$ and increased amount of glucose; PBS-Phosphate buffered saline (PBS) according to Dulbecco (SIGMA Cell Culture Catalogue 1996, Product no. D 8662 or D 5780) with $NaHCO_3$, Tricine, Glucose and Neomycin.

Example 1

Comparative small scale experiments were performed in small flasks (volume 100 ml)with the following media (40 ml ): EMEM (Eagle's minimal essential medium ) supplied by BioNative AB, Umea, Sweden, EMEM supplied by GIBCO and the inventive medium without L-methionine (BNL). The compositions used are presented in Table 1.

TABLE 1

Composition of different media
COMPARISON BETWEEN EMEM/BNL/GIBCO
(tests performed in small flasks) The table shows the difference in composition between two commercially available media and the inventive medium without methionine.

| Component | EMEM (mg/liter) | BNL (mg/liter) | GIBCO (mg/liter) |
|---|---|---|---|
| Calcium Chloride anhydrate | | | 200.00 |
| Calcium Chloride 2 hydrate | 200.00 | 200.00 | |
| Potassium Chloride | 400.00 | 400.00 | 400.00 |
| Magnesium Chloride, anhydrate | | | 97.67 |
| Magnesium Chloride, 6 hydrate | 200.00 | 200.00 | |
| Sodium Chloride | 6800.00 | 6800.00 | 6800.00 |
| Sodium Dihydrogen Phosphate, 2 hydrate | 105.00 | 105.00 | 140.00 |
| $NaHCO_3$ | 750.00 | 750.00 | 750.00 |
| Tricine | 3000.00 | 1500.00 | 3000.00 |
| D-Glucose | 5000.00 | 5000.00 | 5000.00 |
| L-Arginine | 126.00 | | |
| L-Arginine.HCl | | | 126.00 |
| L-Cystine | 25.00 | | |
| L-Cystine.2 HCl | | | 31.29 |
| L-Glutamine | 292.00 | | 292.00 |
| L-Histidine | 42.00 | | |
| L-Histidine.HCl.$H_2O$ | | | 42.00 |
| L-Isoleucine | 52.00 | | 52.00 |
| L-Leucine | 52.00 | | 52.00 |

TABLE 1-continued

Composition of different media
COMPARISON BETWEEN EMEM/BNL/GIBCO
(tests performed in small flasks) The table shows the difference
in composition between two commercially available media and the
inventive medium without methionine.

| Component | EMEM (mg/liter) | BNL (mg/liter) | GIBCO (mg/liter) |
|---|---|---|---|
| L-Lysine, HCl | 73.00 | | 72.50 |
| L-methionine | 15.00 | | 15.00 |
| L-Phenylalanine | 32.00 | | 32.00 |
| L-Threonine | 48.00 | | 48.00 |
| L-Tryptophan | 10.00 | | 10.00 |
| L-Valine | 46.00 | | 46.00 |
| L-Tyrosine | 52.00 | | |
| L-Tyrosine (disodium salt) | | | 51.90 |
| D-Ca Pantothenate | 1.00 | | 1.00 |
| Choline Chloride | 1.00 | | 1.00 |
| i-Inositol | 2.00 | | 2.00 |
| Nicotinamide | 1.00 | | 1.00 |
| Pyridoxin HCl | 1.00 | | 1.00 |
| Riboflavin | 0.10 | | 0.10 |
| Thiamine HCl | 1.00 | | 1.00 |
| Folic Acid | 1.00 | | 1.00 |

Table 1 shows the composition of the inventive medium without L-methionine (BNL) in comparison with two common, more complex commercially available media. When used for the production of natural interferon alpha the media are also supplemented with agamma-plasma (Cantell, 1978) (final concentration about 4%), neomycin sulphate solution 10% (0.25 ml/l) and priming (interferon-alpha added to a final concentration of 100 IU/ml). The interferon alpha yields obtained with these media are shown in Table 2.

Human leukocytes were obtained from buffy coats from different blood centres. The leukocytes were purified in several steps according to Cantell (1981) before incubated in different media. First, the blood bags were cut open and emptied. The blood was then centrifuged and the plasma fraction and the red blood cell (RBC) fraction were separated. The remaining leukocyte containing fraction was subjected to lysis (10 minutes) by adding 2 parts 0.8% $NH^4Cl$ to one part leukocyte fraction. After centrifugation of the lysate, the supernatant containing mainly lysed RBC was discarded and the leukocyte cells were recovered. This lysation and centrifugation step was repeated once and the resulting leukocyte suspension was added to the different media in equal amounts. The media was also supplemented with agamma-plasma (final concentration about 4% v/v), neomycin sulphate solution 10% (0.25 ml/liter) and priming (100 IU interferon alpha/ml medium).

Agamma-plasma was prepared by centrifugation of separated plasma fractions recovered from several batches and then by precipitation of the supernatant through adding one part of 30% (w/w) Polyethylene glycol 6000(Macrogol 6000) to four parts plasma. The mixture was centrifuged and the supernatant (agamma-plasma) was recovered. The precipitate, which contains IgG was discarded.

A 40 ml leukocyte suspension was primed with interferon and incubated at 37.0° C. with magnetic stirring. After 1.5 hours Sendai virus is added. The incubation is continued for about 16 hours. Cells and debris were removed by centrifugation and the supernatant was recovered and its interferon concentration determined by an ELISA method. The Enzyme Linked Immunosorbent Assay (ELISA) is used for the quantitative analysis of Interferon α (IFN-α). The ELISA-standard is calibrated against the international reference preparation 69/19. A parallel incubation in EMEM was used as reference. The results are presented in Table 2.

TABLE 2

Results from the tests with different media (%)
(EMEM/BNL/GIBCO, tests performed in small flasks)
The table shows the results of interferon yield in percentage in
comparison of two commercially available media and the inventive
medium without methionine has been used for interferon production
in small scale. The EMEM result is set to 100% interferon yield.

| | EMEM | BNL | GIBCO |
|---|---|---|---|
| Test 1 | 100 | | 97 |
| Test 2 | 100 | | 109 |
| Test 3 | 100 | | 89 |
| Test 4 | 100 | | 87 |
| Test 5 | 100 | 108 | 99 |
| Test 6 | 100 | 82 | 97 |
| Test 7 | 100 | 94 | 98 |
| Test 8 | 100 | 102 | 86 |
| Test 9 | 100 | 77 | |
| Test 10 | 100 | 104 | |
| Test 11 | 100 | 86 | |
| Test 12 | 100 | 85 | |
| Test 13 | 100 | 95 | |
| Test 14 | 100 | 77 | 87 |
| Test 15 | 100 | 104 | |
| Test 16 | 100 | 79 | 87 |
| Test 17 | 100 | 86 | 87 |
| % of ref (EMEM) | 100 | 91 | 93 |
| SD | | 11, 1 | 7, 5 |
| No of test | | 13 | 11 |

Example 2

Comparative experiments were also performed in small flasks with other media, which are similar to the BNL medium). The compositions used and yields are presented in Table 3. The leukocytes used in Example 2 were prepared in the same way as in Example 1

TABLE 3

COMPARISON BETWEEN EMEM/BNL/CM/CMV/PBS
(according to Dulbecco)

| | EMEM (g/liter) | BNL (g/liter) | CM (g/liter) | CMV (g/liter) | PBS (g/liter) |
|---|---|---|---|---|---|
| $CaCl_2 \times 2H_2O$ | 0.2 | 0.2 | – | – | 0.133 |
| KCl | 0.4 | 0.4 | 0.2 | 0.2 | 0.2 |
| $MgCl_2 \times 6H_2O$ | 0.2 | 0.2 | – | – | 0.1 |
| NaCl | 6.8 | 6.8 | 8.0 | 8.0 | 8.0 |
| $NaH_2PO_4 \times 2H_2O$ | 0.105 | 0.105 | – | – | – |
| Glucose | 5.0 | 5.0 | 1.0 | 5.0 | 5.0 |
| $KH_2PO_4$ | – | – | – | – | 0.2 |
| $Na_2HPO_4 \times 2H_2O$ | – | – | – | – | 1.42 |
| Tricine | 3.0 | 1.5 | 3.0 | 1.5 | 1.5 |
| $NaHCO_3$ | 0.75 | 0.75 | 1.0 | 0.75 | 0.75 |
| Neomycin 10% | 0.25 | 0.25 | 0.25 | 0.25 | 0.25 |
| Amino acids | + | – | – | – | – |
| Vitamin sol. | + | – | – | – | – |
| Folic acid sol. | + | – | – | – | – |
| L-Glutamine | 0.3 | – | 0.3 | – | – |
| Test 1 (%) | 100 | 104 | | 9 | |
| Test 2 (%) | 100 | 27 | 17 | 64 | |

Table 3 shows the interferon-alpha yields obtained with the inventive medium without L-methionine (BNL) in comparison with more complex, commercially available medium (EMEM) and three other simplified media similar to the BNL-medium. One is according to Cantell (1978) (named CM), another is a variant thereof (named CMV) and the third is PBS according to Dulbecco.

Example 3

Tests with different amounts of L-methionine in small scale. Table 4 shows the results from tests of different amounts of L-methionine in BNLM medium. The leukocytes used in Example 3 were prepared in the same way as in Example 1.

TABLE 4

Results from tests of different amounts of L-methionine in BNL in small flasks

|  | BNL | BNLM 15 mg of L-met | BNLM 150 mg of L-met | BNLM 500 mg of L-met | BNLM 1000 mg of L-met | BNLM 2000 mg of L-met |
|---|---|---|---|---|---|---|
| IFN-concentrations measured by an ELISA-method (IU/ml): | | | | | | |
| Test 1 | 67000 | 80000 | 68000 | 67000 | — | 64000 |
| Test 2 | 89000 | 93000 | 85000 | 75000 | 73000 | 66000 |
| Test 3 | 72000 | 74000 | 66000 | 61000 | 60000 | — |
| Yields: | | | | | | |
| Test 1 | 100 | 118 | 101 | 100 | — | 94 |
| Test 2 | 100 | 105 | 96 | 84 | 82 | 74 |
| Test 3 | 100 | 102 | 92 | 85 | 83 | — |

Table 4 shows the interferon-alpha yields obtained with the inventive mediium with L-methionine (BNLM) in different amounts in comparison with the inventive medium without L-methionine. The experiments were performed in small scale, 40 ml medium. The upper panel in Table 4 shows the results of interferon concentrations from three tests where the amount of methionine has been varied. The lower panel shows the corresponding yield in percentage. The inventive medium without methionine result is set to 100% interferon yield.

Example 4

Comparative incubations were performed in pilot scale fermentors (Belach Bioteknik AB, volume 3 l) with different amounts of L-methionine in BNLM medium. The leukocytes used in Example 4 were prepared in the same way as in Example 1. The results are presented in Table 5. The interferon alpha secreted from the leukocytes out into the medium was purified by immunoaffinity chromatography and the purified interferon proteins were analysed by reverse-phase high performance liquid chromatography (RP-HPLC). Shown in FIG. 1 are the HPLC chromatogram from purified samples of interferon produced by leukocytes incubated in BNL medium supplemented with 500 mg/l of L-methionine (lower panel) and from interferon produced in medium without L-methionine (upper panel). The stationary phase in the separating column consists of small uniform particles of surface-modified silica. Proteins or other molecules interact with the stationary phase through hydrophobic interactions. They can be selectively eluted from the column by increasing the amount of organic modifier (acetonitrile) in the mobile phase. A silica with coupled C4(butyl) groups has been found to be useful for the separation of alpha interferon subtypes.

The eluted subtypes display a characteristic peak-pattern in the chromatogram. A major peak eluting at about 50 min constitutes IFN-$\alpha$1. A series of smaller peaks eluting with retention times 0.6 to 0.9 relative to the IFN-$\alpha$1 peak comprises the other IFN-$\alpha$ subtypes in the product. The splitting of peaks, which is most likely due to oxidation of methionine residues in the proteins, is decreased or undetectable when L-methionine is added to the medium. The effect is most pronounced for interferon subtypes alpha 1 and alpha 14(see FIG. 1, upper panel).

TABLE 5

Results from tests of different amounts of L-methionine in BNL in laboratory fermentors

|  | BNL | BNLM 15 mg of L-met | BNLM 75 mg of L-met | BNLM 150 mg of L-met | BNLM 500 mg of L-met |
|---|---|---|---|---|---|
| IFN-concentrations measured by an ELISA-method (IU/ml): | | | | | |
| Test 1 | 94000 | 98000 | — | 92000 | 88000 |
| Test 2 | 116000 | 108000 | — | 99000 | 97000 |
| Test 3 | 83000 | — | — | 84000 | 76000 |
| Test 4 | 100000 | — | 93000 | — | — |
| Yields: | | | | | |
| Test 1 | 100 | 105 | — | 99 | 94 |
| Test 2 | 100 | 93 | — | 85 | 84 |
| Test 3 | 100 | — | — | 101 | 92 |
| Test 4 | 100 | — | 93 | — | — |

Example 5

The trial in Example 4 was repeated with one exception. After incubation, 500 mg methionine/l was added to the BNL medium without L-methionine when the crude interferon was harvested. Shown in FIG. 2 are the HPLC chromatogram from purified samples of interferon produced by leukocytes incubated in BNL medium supplemented with 500 mg/l of L-methionine (upper panel) and from interferon produced in medium without L-methionine (lower panel) but with 500 mg/l of L-methionine added when harvesting. As can be seen, addition of methionine after incubation gives no effect on the interferon. The splitting of peaks remains. It is obvious that the methionine has to be present during incubation.

What is claimed is:

1. A nutrient medium for protein producing cells, wherein said medium consists of the following components: an aqueous physiological saline solution containing $Ca^{2+}$, $K^+$, $Mg^{2+}$ and $Na^+$, an energy source, a pH buffer, agamma-plasma, and methionine in an amount greater than 0.015 g/liter and not more than 2.0 g/liter.

2. A nutrient medium according to claim 1, wherein the medium consists essentially of the following composition (g/l):

| | |
|---|---|
| $CaCl_2 \times 2H_2O$ | 0.13–0.35 |
| KCl | 0.2–0.5 |
| $MgCl_2 \times 6H_2O$ | 0–0.5 |
| NaCl | 5.0–8.0 |
| $NaH_2PO_4 \times 2H_2O$ | 0–0.15 |
| Glucose | 1.0–7.0 |
| Tricine | 1.5–3.0 |
| $NaHCO_3$ | 0.5–3.0 |
| Neomycin 10% | 0–0.25 |
| Methionine | 0.015–2.0, and |
| Agamma-plasma | 1.0–10% (v/v). |

3. A nutrient medium according to claim 1, wherein the medium consists essentially of the following composition (g/l):

| | |
|---|---|
| $CaCl_2 \times 2H_2O$ | 0.13–0.2 |
| KCl | 0.2–0.4 |
| $MgCl_2 \times 6H_2O$ | 0–0.2 |
| NaCl | 6.8–8.0 |
| $NaH_2PO_4 \times 2H_2O$ | 0–0.105 |
| Glucose | 1.0–5.0 |
| Tricine | 1.5–3.0 |
| $NaHCO_3$ | 0.75–1.0 |
| Neomycin 10% | 0–0.25 |
| Methionine | 0.015–2.0, and |
| Agamma-plasma | 3.0–5% (v/v). |

4. A nutrient medium according to claim 1, having a methionine content of 0.050–2.0 g/l.

5. A nutrient medium according to claim 1, having a methionine content of 0.050–0.100 g/l.

6. A nutrient medium according to claim 1, wherein the medium consists essentially of the following composition (g/l):

| | |
|---|---|
| $CaCl_2 \times 2H_2O$ | 0.2 |
| KCl | 0.4 |
| $MgCl_2 \times 6H_2O$ | 0.2 |
| NaCl | 6.8 |
| $NaH_2PO_4 \times 2H_2O$ | 0.105 |
| Glucose | 5.0 |
| Tricine | 1.5 |
| $NaHCO_3$ | 0.75 |
| Neomycin 10% | 0.25 |
| Methionine | 0.075, and |
| Agamma-plasma | 4% (v/v). |

7. A nutrient medium according to claim 1 that additionally includes an antibiotic.

8. A nutrient medium according to claim 2, wherein the medium consists essentially of the following composition (g/l):

| | |
|---|---|
| $CaCl_2 \times 2H_2O$ | 0.13–0.2 |
| KCl | 0.2–0.4 |
| $MgCl_2 \times 6H_2O$ | 0–0.2 |
| NaCl | 6.8–8.0 |
| $NaH_2PO_4 \times 2H_2O$ | 0–0.105 |
| Glucose | 1.0–5.0 |
| Tricine | 1.5–3.0 |
| $NaHCO_3$ | 0.75–1.0 |
| Neomycin 10% | 0–0.25 |
| Methionine | 0.015–2.0, and |
| Agamma-plasma | 3.0–5% (v/v). |

9. A nutrient medium according to claim 7, wherein the medium consists essentially of the following composition (g/l):

| | |
|---|---|
| $CaCl_2 \times 2H_2O$ | 0.13–0.2 |
| KCl | 0.2–0.4 |
| $MgCl_2 \times 6H_2O$ | 0–0.2 |
| NaCl | 6.8–8.0 |
| $NaH_2PO_4 \times 2H_2O$ | 0–0.105 |
| Glucose | 1.0–5.0 |
| Tricine | 1.5–3.0 |
| $NaHCO_3$ | 0.75–1.0 |
| Neomycin 10% | 0–0.25 |
| Methionine | 0.015–2.0, and |
| Agamma-plasma | 3.0–5% (v/v). |

10. A nutrient medium according to claim 2, wherein the medium consists essentially of the following composition (g/l):

| | |
|---|---|
| $CaCl_2 \times 2H_2O$ | 0.2 |
| KCl | 0.4 |
| $MgCl_2 \times 6H_2O$ | 0.2 |
| NaCl | 6.8 |
| $NaH_2PO_4 \times 2H_2O$ | 0.105 |
| Glucose | 5.0 |
| Tricine | 1.5 |
| $NaHCO_3$ | 0.75 |
| Neomycin 10% | 0.25 |
| Methionine | 0.075 and |
| Agamma-plasma | 4% (v/v). |

11. A nutrient medium according to claim 3, wherein the medium consists essentially of the following composition (g/l):

| | |
|---|---|
| $CaCl_2 \times 2H_2O$ | 0.2 |
| KCl | 0.4 |
| $MgCl_2 \times 6H_2O$ | 0.2 |
| NaCl | 6.8 |
| $NaH_2PO_4 \times 2H_2O$ | 0.105 |
| Glucose | 5.0 |
| Tricine | 1.5 |
| $NaHCO_3$ | 0.75 |
| Neomycin 10% | 0.25 |
| Methionine | 0.075, and |
| Agamma-plasma | 4% (v/v). |

12. A nutrient medium according to claim 4, wherein the medium consists essentially of the following composition (g/l):

| | |
|---|---|
| CaCl$_2$ × 2H$_2$O | 0.2 |
| KCl | 0.4 |
| MgCl$_2$ × 6H$_2$O | 0.2 |
| NaCl | 6.8 |
| NaH$_2$PO$_4$ × 2H$_2$O | 0.105 |
| Glucose | 5.0 |
| Tricine | 1.5 |
| NaHCO$_3$ | 0.75 |
| Neomycin 10% | 0.25 |
| Methionine | 0.075 and |
| Agamma-plasma | 4% (v/v). |

13. A nutrient medium according to claim 5, wherein the medium consists essentially of the following composition (g/l):

| | |
|---|---|
| CaCl$_2$ × 2H$_2$O | 0.2 |
| KCl | 0.4 |
| MgCl$_2$ × 6H$_2$O | 0.2 |
| NaCl | 6.8 |
| NaH$_2$PO$_4$ × 2H$_2$O | 0.105 |
| Glucose | 5.0 |
| Tricine | 1.5 |
| NaHCO$_3$ | 0.75 |
| Neomycin 10% | 0.25 |
| Methionine | 0.075, and |
| Agamma-plasma | 4% (v/v). |

14. A nutrient medium according to claim 7, wherein the medium consists essentially of the following composition (g/l):

| | |
|---|---|
| CaCl$_2$ × 2H$_2$O | 0.2 |
| KCl | 0.4 |
| MgCl$_2$ × 6H$_2$O | 0.2 |
| NaCl | 6.8 |
| NaH$_2$PO$_4$ × 2H$_2$O | 0.105 |
| Glucose | 5.0 |
| Tricine | 1.5 |
| NaHCO$_3$ | 0.75 |
| Neomycin 10% | 0.25 |
| Methionine | 0.075, and |
| Agamma-plasma | 4% (v/v). |

15. A method for culturing cells which produce protein comprising the step of incubating the cells in the nutrient medium of claim 1.

16. A method for culturing cells which produce protein comprising the step of incubating the cells in the nutrient medium of claim 7.

17. The method according to claim 16, wherein said cells producing protein are leukocytes.

18. The method according to claim 17, wherein said protein is interferon.

* * * * *